United States Patent [19]

Lündt et al.

[11] Patent Number: 4,598,065

[45] Date of Patent: Jul. 1, 1986

[54] USE OF PEPTIDES AS MEDICAMENTS AND CERTAIN NOVEL PEPTIDES

[75] Inventors: Behrend F. Lündt, Kokkedal; Karin D. Jorgensen, Vedbaek; Nils L. Johansen, Copenhagen; Frederik C. Gronvald, Vedbaek; Erik K. Frandsen, Charlottenlund; Alister J. Moody, Lyngby; Jan Markussen, Herlev, all of Denmark

[73] Assignee: Novo Industri A/S, Denmark

[21] Appl. No.: 279,153

[22] Filed: Jun. 30, 1981

[30] Foreign Application Priority Data

Jul. 1, 1980 [DK] Denmark ............................ 2831/80

[51] Int. Cl.$^4$ .............................................. A61K 37/02
[52] U.S. Cl. ........................................ 514/12; 514/13
[58] Field of Search .................. 260/112.5 R; 514/13, 514/12

[56] References Cited

U.S. PATENT DOCUMENTS 3,642,763  2/1972  Wunsch et al.
3,715,345  2/1973  Smith
3,875,138  4/1975  Jackson
4,221,777  9/1980  Nishino

FOREIGN PATENT DOCUMENTS 3039122  4/1981  Fed. Rep. of Germany
2062644  5/1981  United Kingdom

OTHER PUBLICATIONS

Abiko et al., *Chem. Pharm. Bull.*, 27(11), 2827–31 (1979).
Fujino et al., *Chem. Pharm. Bull.*, 26(2), 539–548 (1978).
Wright et al., *J. of Biological Chem.*, 253, 6338 (1978).
Frandsen et al., *Hoppe-Seyler's Z. Physiol. Chem.*, 362, 665–675 (1971).
Jorgensen et al., *European J. of Pharm.*, 90 (No. 4), 315–323 (1983).
Goldfine et al., *J. of Biol. Chem.*, 247 (No. 4), 1211–1218 (1972).
Bromer, *Metabolism Clinical and Experimental*, XXV, 1315–16 (1976).
Schröder et al., *The Peptides*, II, Academic Press, N.Y., 254–260 (1966).
*Chemical Abstracts*, 70, 2028 (1969), Abst. No. 20330f.
Spiegel et al., *Activity of Modified Glucogon*, 85, 638–643 (1969).
Rodbell et al., *Proc. Nat. Acad. Sci. USA*, 68 (No. 5), 909–913 (1971).
Assan et al., *Diabetes*, 21 (No. 8), 843–855 (1972).
Epand et al., *Canadian J. of Physiol. & Pharm.* 51, 243–8 (1973).
Ross et al., *Biochemistry*, 16 (No. 24), 5398–5402 (1977).
Deranleau et al., *J.A.C.S.*, 100: 6, 1913–1917 (1978).

*Primary Examiner*—Delbert R. Phillips
*Assistant Examiner*—F. T. Moezie
*Attorney, Agent, or Firm*—Fidelman, Wolffe & Waldron

[57] ABSTRACT

Certain peptides containing the glucagon$_{1-21}$ peptide chain His-Ser-Gln-Gly-Thr-Phe-Thr-Ser-Asp-Tyr-Ser-Lys-Tyr-Leu-Asp-Ser-Arg-Arg-Ala-Gln-Asp, usable as a medicament or a diagnostic; the peptide exerts a spasmolytic effect and an inhibitory effect on gastric acid secretion similar to glucagon with not more than a negligible metabolic effect. Some of the glucagon fragments are novel compounds.

4 Claims, No Drawings

USE OF PEPTIDES AS MEDICAMENTS AND CERTAIN NOVEL PEPTIDES

The present invention relates to the use of peptides of the general Formula I $$R^1-R^2 \quad (I)$$

wherein $R^1$ represents

His—Ser—Gln—Gly—Thr—Phe—Thr—Ser—Asp—Tyr—
  5                                       10

Ser—Lys—Tyr—Leu—Asp—Ser—Arg—Arg—Ala—
  15

Gln—Asp—,
  20 and $R^2$ represents OH, the peptide chain

—Phe—Val—Gln—Trp—Leu
  25 or a fragment thereof, of —Met—Asn—Thr or a fragment thereof. By fragment is intended a corresponding peptide chain which is identical with one of the two last-mentioned peptide chains with the proviso that one or more of the amino acid(s) has/have been omitted. Compounds of Formula I and non-toxic salts thereof show interesting and surprising pharmacological properties.

Glucagon, a polypeptide hormone consisting of 29 amino acids, is known to possess several pharmacological effects. The use of glucagon for the treatment of hypoglycemia is based upon its metabolic effects. Furthermore, glucagon exerts a spasmolytic effect on smooth muscle and an inhibitory effect on gastric acid secretion. It has now surprisingly been found that compounds of Formula I cause a similar spasmolytic effect and a similar inhibitory effect on gastric acid secretion as equal quantities of glucagon, although compounds of Formula I cause not more than negligible metabolic effect i.e., none to minor. Hence, compounds of Formula I are believed to be superior to glucagon when only a spasmolytic effect or an inhibition of gastric acid secretion is desired.

Glucagon$_{1-21}$, glucagon$_{1-26}$ and des(22-26)-glucagon, all peptides within Formula I and corresponding to $R^1-R^2$, have been found to have almost the same potency as glucagon as regards inhibitory effect on the amplitude of the contractions of the electrically stimulated guinea pig ileum in vitro. $10^{-5}$M glucagon caused $83\pm4\%$ ($\bar{X}\pm$sd, N=3) ihibition compared to $78\pm5\%$ for glucagon$_{1-21}$. The effects of $10^{-6}$M was $50\pm3\%$ and $52\pm5\%$, respectively, and of $10^{-7}$M: $27\pm3\%$ for either peptide.

Furthermore, glucagon$_{1-21}$ has almost the same potency as glucagon with respect to reducing effect on intestinal motility in rabbits in vivo. Each of 100 to 200 μg glucagon and 77 to 154 μg glucagon$_{1-21}$ administered intravenously as a bolus to anesthesized rabbits of 2.5 to 3.0 kg body weight caused an inhibition of intestinal motility beginning one minute after the administration and lasting from about ten minutes.

The metabolic effects of glucagon$_{1-21}$, glucagon$_{1-26}$ and des(22-26)-glucagon, as exemplified by their lipolytic effect on rat free fat cells in vitro and their effect on the activation of the adenylate cyclase in vitro, are negligible compared with the metabolic effects of glucagon. No metabolic effects have been found after administration to rats in vivo.

It has been shown that glucagon releases insulin from the isolated perfused rat pancreas, but glucagon$_{1-21}$ has no such effect when it is infused to the same concentration as glucagon. Furthermore, glucagon$_{1-21}$ (contrary to glucagon) does not cause hyperglycemia or release insulin in vivo in rats.

In cats with chronic gastric fistulas glucagon$_{1-21}$ as well as glucagon inhibit pentagastrin stimulated gastric acid secretion. 1 μg/kg pentagastrin subcutaneously administered to gastric fistula cats caused an increase in gastic acid secretion of $856\pm71$ μEq (Eq designates equivalent) acid ($\bar{X}\pm$S.E.M., N=18). When 2 μg/kg glucagon$_{1-21}$ was administered subcutaneously at the same time as 1 μg/kg pentagastrin the increase in acid output was only $417\pm104$ μEq acid (N=6).

Glucagon$_{1-21}$ and glucagon are almost equipotent as regards relaxing effect on a submaximally contracted rabbit gall bladder preparation in vitro, and both compounds cause an increase in gall flow in rats in vivo. When a gall bladder strip was contracted with 0.1 μg/ml cholecystochinin octapeptide $10^{-6}$M glucagon caused 39% relaxation and $10^{-6}$M glucagon$_{1-21}$ caused 41% relaxation. The $ED_{50}$ value was for both peptides $2.7\times10^{-6}$M. Therefore, compounds of Formula I may have a potential utility in the treatment of biliary tract, and, because of their general spasmolytic properties, possibly urinary calculi patients. As regards this utility, the fact that compounds of Formula I have no or minor, negligible metabolic effect is believed to be a considerable advantage.

Hence a compound of Formula I or a non-toxic salt thereof may be used as a therapeuticum or a diagnosticum. The indication areas for use of the compounds of Formula I and salts thereof in therapy will be, for example, biliary tract and urinary tract calculi, spasms in the digestive system and gastro-duodenal ulcers. The compounds of Formula I and non-toxic salts thereof may be used for diagnostic purposes in investigational techniques such as radiology (X-ray examination), endoscopy (direct observation of the gastro-intestinal tract), and hysterosalpingographia. The dosage which will, of course, depend upon the purpose for administering the compound of Formula I or its non-toxic salt may be from 0.1-1000 μg/kg of body weight, and comparably the dosage form unit may contain from 7.5-75,000 μg per dosage unit; preferred are 7.5-7500 μ/g units.

Compounds of Formula I are converted into pharmaceutical preparations and administered, preferably to humans, in analogy with known methods.

Compounds of Formula I and salts thereof can, as diagnosticum, be used in analogy with the use of glucagon for the same purpose.

Compounds of Formula I and pharmaceutically acceptable salts thereof can be administered intravenously, intramuscularly or subcutaneously at dosages in the range of from about 1 to 1000 μg/kg body weight, preferably from about 10 to 100 μg/kg body weight, although a lower or higher dosage may be administered. The required dosage will depend on the severity on the condition of the patient and the duration of the treatment. A higher dosage may be used for biliary tract and urinary tract calculi patients and gastro-duodenal ulcer patients and, in these cases, multiple dosages of the compounds may be administered, for example, parenterally (for example, as a continuous infusion) or by the nasal or rectal route.

Compounds of Formula I may possibly be administered orally, e.g., by the use of special additives.

For the purpose of parenteral administration, compounds of Formula I are dissolved in distilled water and the pH value is adjusted to about 6–8. In order to facilitate lyophilization lactose may be added to the solution. The solution is sterile filtered and filled in vials. Thereafter, the solutions are lyophilized and the vials are sealed under aseptic conditions.

For nasal administration, a solution in a nasal spraying device or nebulisator is used. The compounds of Formula I are dissolved in distilled water, the pH value is adjusted to about 6–8 by adding sodium phosphate and citric acid as buffer. Sodium chlorine, sorbitol and glycerol are added to obtain an isotonic solution with a suitable viscosity. The solution is administered by the use of a suitable nebulisator or plastic spray. The solution may also contain pharmaceutically acceptable (known) preservative and (known) surfactant.

For the purpose of nasal administration by the use of dose aerosol spray the peptides are mixed with suitable constituents as described above and a mixture of volatile halogencarbons, i.e., monofluorotrichloromethane, difluorodichloromethane and tetrafluorodichloroaethane, in order to obtain a mixture with a vapor pressure producing a well defined single dose when the mixture is administered by the use of a dose aerosol spray.

The compounds of Formula I are preferably used by nasal administration in a dosage range between about 0.1 and 100 μg/kg body weight, preferably between 1 and 10 μg/kg body weight, per single dose. This dose could be administered several times per day.

For the purpose of rectal administration, suppositories are produced by admixing one or more of the peptides of Formula I with an inactive constituent such as cocoa butter or with a base such as Polysorbate 85, propylene glycol monostearate and white beeswax.

Compounds of Formula I and salts thereof can be prepared by methods which are generally known in peptide synthesis. Briefly, compounds of Formula I can be built up from a protected glucagon fragment, e.g., protected glucagon$_{1-15}$, and a protected peptide containing the remaining amino acids in the desired peptide compound of Formula I. The preparation of protected glucagon$_{1-15}$ is described in Res. Discl. 1979, 247. Peptides containing more than amino acids Nos. 16–21 in glucagon can be built up from a protected glucagon fragment, e.g., protected glucagon$_{16-21}$, and a protected peptide containing the remaining amino acids. The use of suitable protecting groups and activations during the peptide synthesis is known to the art. It is desired to use protecting groups which can easily be removed.

Thus, glucagon$_{1-21}$, glucagon$_{1-26}$ and des(22–26) glucagon can be prepared by coupling the protected glucagon fragment:

Adoc—His(Adoc)—Ser(Bu$^t$)—Gln—Gly—Thr(Bu$^t$)—Phe—    (II)
5

Thr(Bu$^t$)—Ser(Bu$^t$)—Asp(OBu$^t$)—Tyr(Bu$^t$)—Ser(Bu$^t$)—
10

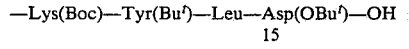

with the protected glucagon fragments:

H—Ser(Bu$^t$)—Arg(HCl)—Arg(HCl)—Ala—Gln—    (III)
20

—Asp(OBu$^t$)—OBu$^t$

H—Ser(Bu$^t$)—Arg(HBr)—Arg(HBr)—Ala—Gln—    (IV)
20

—Asp(OBu$^t$)—Phe—Val—Gln—Trp—Leu—OBu$^t$
25 or H—Ser(Bu$^t$)—Arg(HBr)—Arg(HBr)—Ala—Gln—    (V)
20

—Asp(OBu$^t$)—Met—Asn—Thr(Bu$^t$)—OBu$^t$ respectively, by the mixed anhydride method using isobutyl chloroformate. The fully protected peptides so obtained can be deprotected under acid conditions, e.g., by treatment with trifluoroacetic acid containing 10% 1,2-ethanedithiol. The crude peptides can be purified by ion-exchange chromatography, e.g., QAE-Sephadex A-25, followed by a desalting procedure, e.g., gel-filtration on Sephadex G-25. The purified peptides can be isolated by lyophilization. The intermediate protected glucagon fragments IV and V can be prepared by coupling, using the mixed anhydride procedure, the protected glucagon fragment:

Bpoc—Ser(Bu$^t$)—Arg(HBr)—Arg(HBr)—Ala—Gln—    (VI)
20

—Asp(OBu$^t$)—OH with the protected glucagon fragments:

H—Phe—Val—Gln—Trp—Leu—OBu$^t$    (VII)
25 or

H—Met—Asn—Thr(Bu$^t$)—OBu$^t$    (VIII)

respectively, whereupon the N-terminal Bpoc group can be removed selectively under mild acid conditions, e.g., by treatment with HCl (0.2N) in methanol/N,N-dimethylformamide.

The protected peptide fragments III, VI, VII and VIII were synthesized by stepwise chain elongation applying conventional procedures such as for example, the active ester or mixed anhydride methods for coupling.

Peptides of Formula I, wherein R$^2$ represents the peptide chain

—Phe—Val—Gln—Trp—Leu
25 or —Met—Asn—Thr in which one or more amino acid(s) has/have been omitted, can be prepared in a similar manner as described above with the exception that or more of the amino acid(s) in question has/have been omitted in the protected peptide fragments VII and VIII.

A process for preparing glucagon$_{1-21}$ has been described in J. Biol. Chem. 247, 2133, by digesting porcine, bovine or sheep glucagon with carboxypeptidase A. Glucagon$_{1-26}$ is known from Metabolism 25, Suppl. 1, 1315.

A preferred subclass of compounds of Formula I is compounds wherein the amino acid sequence is identical with a continuous part of the amino acid sequence of glucagon. As examples of specific compounds, within this class of compounds, compounds of Formula I, wherein R$^2$ is Phe, Val, Gln, Trp, Leu, Met, Asn or Thr can be mentioned. A preferred compound of Formula I is glucagon$_{1-21}$ because it shows superior pharmacological properties and because it can easily be obtained, e.g., from natural glucagon.

Furthermore, the present invention relates to compounds of the general Formula I'

$$R^1—R'^2 \qquad (I')$$

wherein
R$^1$ is as defined above, and
R$'^2$ has the same meaning as R$^2$ provided R$'^2$ does not represent —Phe—Val—Gln—Trp—Leu
25 or OH, or a salt thereof.

Briefly, compounds of Formula I' may be prepared by treating a compound of the general formula $$R^3—R^4—OBu^t \qquad (IX)$$

wherein
R$^3$ represents

Adoc—His(Adoc)—Ser(Bu$^t$)—Gln—Gly—Thr(Bu$^t$)—Phe—
5

Thr(Bu$^t$)—Ser(Bu$^t$)—Asp(OBu$^t$)—Tyr(Bu$^t$)—Ser(Bu$^t$)—
10

Lys(Boc)—Tyr(Bu$^t$)—Leu—Asp(OBu$^t$)—Ser(Bu$^t$)—Arg(HX)—
15

Arg(HX)—Ala—Gln—Asp(OBu$^t$)—
20

R$^4$ represents the peptide moiety

—Phe—Val—Gln—Trp—Leu—
25 from which one or more of the amino acid(s) has/have been omitted, the peptide moiety —Met—Asn—Thr-(Bu$^t$)— or corresponding peptide moieties which are identical with said moiety with the proviso that one or more of the amino acid(s) has/have been omitted, and X represents chlorine or bromine, with an acid such as trifluoroacetic acid.

As examples of non-toxic salts of compounds of Formula I, for example, sodium, potassium, magnesium, calcium, and zinc salts and acid addition salts with organic or inorganic acids such as formic acid, methansulfonic acid, hydrochloric acid and sulphuric acid can be mentioned. Preferred salts of compounds of Formula I are the physiologically and pharmaceutically acceptable salts.

The present invention also relates to a pharmaceutical composition comprising a compound of Formula I or a pharmaceutically acceptable salt thereof and a pharmaceutically acceptable carrier. Diluent(s) preferably water, and/or excipient(s) may form part or all of the carrier. As examples of other frequent carrier components, conventional preservatives e.g., methyl or propyl p-hydroxybenzoate, and sodium chloride can be mentioned.

The nomenclature used herein complies with that stated in J. Biol. Chem. 247, 977, and Biochem. J. 104, 17. However, for the sake of brevity, glucagon-(1-21)-heneicosapeptide herein has been designated glucagon-$_{1-21}$; glucagon-(1-26)-hexacosapeptide has been designated glucagon$_{1-26}$ and des-pentapeptide-(22-26)-glucagon has been designated des(22-26)-glucagon. Bpoc represents 1-(biphenyl-4-yl)-1-methylethoxy-carbonyl, Adoc represents 1-adamantyloxycarbonyl, Bu$^t$ represents tertiary butyl, and Boc represents tert-butyloxycarbonyl.

The following examples which, however, are not intended to be limited, are presented to illustrate the invention.

EXAMPLE 1 des(22-26)glucagon 1 g of

Adoc—His(Adoc)—Ser(Bu$^t$)—Gln—Gly—Thr(Bu$^t$)—Phe—
5

Thr(Bu$^t$)—Ser(Bu$^t$)—Asp(OBu$^t$)—Tyr(Bu$^t$)—Ser(Bu$^t$)—
10

Lys(Boc)—Tyr(Bu$^t$)—Leu—Asp(OBu$^t$)—Ser(Bu$^t$)—
15

Arg(HBr)—Arg(HBr)—Ala—Gln—Asp(OBu$^t$)—Met—Asn—
20

Thr(Bu$^t$)—OBu$^t$ is dissolved in 25 ml of trifluoroacetic acid containing 10% 1,2-ethanedithiol and the reaction mixture is left at 15° C. for 3 hours. Thereafter, 200 ml of tetrahydrofuran is added slowly and the precipitate is isolated, washed with tetrahydrofuran and dried in vacuo. The resulting product may be purified by ion-exchange chromatography on QAE Sephadex A-25 and desalted by gel-filtration on Sephadex G-25.

EXAMPLE 2

A preparation of parenteral administration containing 1 mg of glucagon$_{1-21}$ per ml may be prepared as follows:

1 g of glucagon$_{1-21}$ and 99 g of lactose are dissolved in 1 liter of distilled water and the pH-value is adjusted to 7.0. The solution is thereafter sterile filtered. The sterile solution is filled in 10 ml vials in such a way that each vial contains 1.0 ml of the solution. Thereafter, the solutions are lyophilized and the vials are sealed under aseptic conditions.

The preparation in any of the vials is to be dissolved in 1.0 ml of sterile, isotonic water before administration.

EXAMPLE 3

A preparation for parenteral administration containing 10 mg of glucagon$_{1-21}$ per ml may be prepared as follows:

10 g of glucagon$_{1-21}$ and 90 g of lactose are dissolved in 1 liter of distilled water and the solution is prepared analogously to the method described in Example 2.

EXAMPLE 4

Rectal suppositories are prepared by admixing 1 mg of glucagon$_{1-21}$ with 4 g of cocoa butter.

EXAMPLE 5

A nasal plastic spray may be prepared as follows:

0.5 g of glucagon$_{1-21}$ is dissolved in about 95 ml of 0.01M phosphate buffer (pH-value: 7.4) which is made isotonic by the addition of glycerol. The solution is preserved by the addition of 0.01% benzalkonium chloride and 0.05% EDTA whereafter 0.5% polyoxysorbate is added. An isotonic phosphate buffer is added in order to give a resulting volume of 100 ml and the solution is sterile filtered. 15 ml of said solution is filed in a blast spray giving 0.5 mg of glucagon$_{1-21}$, when activated.

Experiment A: Spasmolytic Effect

One male rabbit weighing 2.56 kg was anaesthetized with nembutal after an overnight fast. The position of the balloon used for measurement of intestinal motility was 1 meter from pylorus in the jejunum. The motility was registered before and after intraveneous administration of 77 µg glucagon$_{1-21}$ in 1 ml 0.9% saline containing 0.1% human serum albumin. The effect obtained was nearly complete atonia of the intestine. The onset of effect was 1 minute after the administration and the duration of effect was 11 minutes.

Experiment B: Spasmolytic Effect

A male rabbit weighing 2.32 kg was treated as described in Experiment A with the following dosages:

77 µg glucagon$_{1-21}$ in 1 ml of the solution stated in Experiment A intravenously caused no detectable spasmolytic effect.

154 µg glucagon$_{1-21}$ in 1 ml of the solution in Experiment A intravenously had a questionable effect. 308 µg glucagon$_{1-21}$ in 1 ml of the above solution had a distinct spasmolytic effect causing nearly complete atonia. The onset of the effect was 2½ minute and the duration of the effect was 6 minutes.

For comparison glucagon was administered to the same rabbit. 200 µg glucagon intravenously had no detectable effect, however, 400 µg gave a distinct effect comparable to the effect caused by 308 µg glucagon$_{1-21}$.

Experiment C: Gastric Acid Inhibitory Effect

In a male cat weighing approx. 4.5 kg equipped with a cronic gastric fistula the gastric acid secretion was stimulated with 4.5 µg pentagastrin (Peptavlon ®) in a volume of 1 ml 0.9% saline containing 1% human serum albumin subcutaneously in the neck. In 8 experiments 1 ml placebo (0.9% saline with 0.1% human serum albumin) was administered subcutaneously through another cannula in the neck at the same time as the administration of pentagastrin. In 2 experiments 9 µg of glucagon$_{1-21}$ in 1 ml of the above solution was administered simultaneously with the administration of pentagastrin. Gastric acid secretion was collected over periods of 15 minutes and titrated with 0.01N NaOH. The increase in acid secretion after the administration of pentagastrin was calculated as µEq acid excreted over 1½ hrs. after the administration subtracting the basal acid secretion before administration of pentagastrin. After administration of 4.5 µg pentagastrin plus placebo the increase in gastric acid secretion was 729±89 µEq acid ($\overline{X}$±S.E.M., N=8). 4.5 µg pentagastrin+9 µg glucagon$_{1-21}$ caused an increase in acid secretion of 238 µEq in one experiment and 231 µEq in another experiment.

Experiment D: Effect on Bile Flow

In rabbits with catheters in the bile duct the administration of glucagon and glucagon$_{1-21}$ caused a decrease in gall flow immediately after the administration, probably reflecting a decrease in the tonus of the gall bladder. This decrease in flow was followed by an increase in bile flow to quantities higher than before the administration reflecting an increase in production of bile.

One rex rabbit weighing 2.0 kg was equipped with a catheter in the bile duct during nembutal anaesthesia on the day before the experiment. On the day of the experiment the bile was collected for periods of 15 minutes.

The results obtained appear from the following table:

| Sampling periods, minutes | 0-15 | 15-30 | 30-45 | 45-60 | 60-75 | 75-90 | 90-105 | 105-120 | 120-135 | 135-150 |
|---|---|---|---|---|---|---|---|---|---|---|
| Amount of bile, ml | 1.20 | 1.50 | 1.40 | 0.20 | 0.25 | 3.30 | 2.80 | 2.00 | 0.40 | 1.65 |
| Sampling periods, minutes | | 150-165 | 165-180 | 180-195 | 195-210 | 210-225 | 225-240 | 240-255 | 255-270 | |
| Amount of bile, ml | | 2.05 | 3.50 | 1.10 | 1.50 | 1.50 | 1.35 | 1.70 | 1.75 | |

After 45 minutes 200 µg glucagon was administered subcutaneously in 1 ml of 0.9% saline containing 0.1% human serum albumin. After 120 minutes 154 µg glucagon$_{1-21}$ was administered subcutaneously in 1 ml of the above solution. After 195 minutes the placebo (vide Experiment C) was administered.

Experiment E: Acute Toxicity Study 10 mg glucagon$_{1-21}$ administered intravenously as a bolus to NMRI mice weighing 20 g (i.e. a dose of 500 mg/kg body weight) and no adverse effects. No deaths occurred.

What we claim is:

1. A method for exerting a spasmolytic effect with not more than negligible metabolic effect which comprises administering to a host in need of such treatment an effective amount of a peptide having the following formula:

$$R^1\text{—}R^2 \tag{I}$$

wherein $R^1$ represents

His—Ser—Gln—Gly—Thr—Phe—Thr—Ser—Asp—Tyr—
                         5                                   10

Ser—Lys—Tyr—Leu—Asp—Ser—Arg—Arg—Ala—
                            15

$$\text{Gln}-\text{Asp}-,$$

and $R^2$ represents OH, Phe, Val, Gln, Trp, Leu, Met, Asn, Thr, the peptide chain $$-\text{Phe}-\text{Val}-\text{Gln}-\text{Trp}-\text{Leu},$$

or —Met—Asn—Thr, or a pharmaceutically acceptable salt of said peptide.

2. A method according to claim 1 comprising administering 1-100 µg/kg of body weight.

3. A method according to claim 2 comprising administering 10-100 µg/kg of body weight intravenously, intramuscularly or subcutaneously.

4. A method according to claim 1, wherein $R^2$ represents OH, Phe, Val, Gln, Trp, Leu, Met, Asn or Thr.

* * * * *